(12) United States Patent
Khaw (10) Patent No.: US 6,746,411 B2
(45) Date of Patent: Jun. 8, 2004

(54) EXITABLE LUMEN GUIDE WIRE SHEATH AND METHOD OF USE

(75) Inventor: Kenneth Khaw, Plainsboro, NJ (US)

(73) Assignee: The University of Medicine and Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 10/072,276

(22) Filed: Feb. 6, 2002

(65) Prior Publication Data

US 2003/0149444 A1 Aug. 7, 2003

(51) Int. Cl.$^7$ ................................................. A61B 5/00
(52) U.S. Cl. ...................................................... 600/585
(58) Field of Search ............................... 606/191–200; 600/434, 585; 623/1.35

(56) References Cited

U.S. PATENT DOCUMENTS 4,988,356 A * 1/1991 Crittenden et al. .......... 606/192
6,129,738 A 10/2000 Lashinski et al.
6,290,710 B1 * 9/2001 Cryer et al. ................ 606/200

OTHER PUBLICATIONS

Abugov et al., *Comparative Analysis of Early and Late Outcomes of Balloon Coronary Angioplasty for Bifurcation Stenoses, Performed by Routine and Two–Guide Methods*, Russian Journal of Radiology No. 4, 1998, 10–14.

Andreoli et al., *Cardiovascular Diseases*, Cecil Essentials of Medicine, 1986, 1–33.

Holmes et al., *Coronary Artery Stents*, JACC vol. 32, No. 5, Nov. 1, 1998:1471–82.

Pinkerton et al., *Complex Coronary Angioplasty: A Technique for Dilatation of Bifurcation Stenoses*. Angiology, The Journal of Vascular Diseases, vol. 36, No. 8, Aug. 1985, 543–548.

Schalcher et al., *To stent or not to stent*, Schweiz. Med Wochenschr. 1999;129:1679–96.

Tan et al., *What You Need to Know–13 Coronary Stenting–13 What's New In the Horizon?* Sisngapore Med. J. 1999; vol. 40(6): 434–437.

PCT International Search Report for International Application No. PCT/US03/03508, dated Jul. 17, 2003, 3 pages.

* cited by examiner

*Primary Examiner*—Kevin T. Truong
(74) *Attorney, Agent, or Firm*—Perkins Coie LLP (57) ABSTRACT

The present invention is directed to an apparatus for and method of treatment or vascular procedures. An exitable lumen guide wire sheath is disclosed and advantages thereof. The exitable lumen guide wire sheath and method may be used as a multiple exitable lumen or single exitable lumen. A method of treatment of multiple branch vascular lesions is disclosed in which a desired branch of a multiple branch lesion may be protected for further procedures by an interventionalist or other practitioner. Other combinations and uses for the disclosed invention will be apparent to those skilled in the art.

27 Claims, 4 Drawing Sheets

EXITABLE LUMEN GUIDE WIRE SHEATH AND METHOD OF USE

FIELD OF THE INVENTION

The invention is directed vascular medical procedures using catheters and/or guide wires.

BACKGROUND OF THE INVENTION

The state of the art in cardiovascular, and vascular procedures in general, is at the forefront of interventional medicine procedures designed to prolong life and add to the quality of life. Interventional medicine, whether performed by an interventionalist specialist or other practitioner, is an advancing and beneficial science. For many people, a healthy and sustained existence is in constant jeopardy due to clogged, narrowed, sclerosed or damaged vasculature. This is especially true of the cardiovasculature and peripheral vasculature. Interventional medicine is designed to address these and other problems.

Commonly, a vessel may become stenotic, or narrowed. One of the most familiar and common etiologies of this stenosis is atherosclerosis. Atherosclerosis is a thickening and hardening of medium and larger arteries with narrowing of the arterial lumen by atherosclerotic plaques; its cause is multifactorial. See, Andreoli, Carpenter, Plum and Smith, *Cecil, Essentials of Medicine* (W. B. Saunders Co. 1986). Other causes of stenosis include injury, syphilis, polyarteritis nodosa, Takayasu's disease, disseminated lupus erythematous, rheumatoid arthritis and other arteritis. Id. There is also continuing evidence that timely Percutaneous Transluminal Coronary Angioplasty (PTCA) is superior to other treatments in patients with acute myocardial infarction. See, Sutsch, Amamn, *To Stent or Not to Stent,* Schweiz. Med. Wochenchr. 1999;

Blood flow volume through a stenotic vessel is slowed and restricted or "backed up" proximal to the stenosis. This can be further complicated by mechanical, chemical and immunologic injury. The intimal surface of the vessel may ulcerate, thrombose and occlude the lumen of the vessel. This leads to decreased nourishment and oxygenation of the distal tissues and can ultimately lead to necrosis.

Further, and consistent with Bernoulli's law, the velocity of the blood flow is inversely proportional to the pressure exerted by the side of the vessel. In other words, the velocity is greatest and the pressure is lowest at the point of maximum stenosis. This fact has important ramifications as the increased velocity leads to increase turbulence in the flow distal to the stenosis. This, in turn, increases the ability of deposits, i.e. atherosclerotic plaques, to adhere to the vascular intima. In a similar phenomenon, plaques tend to occur at arterial bifurcations, again due to the turbulent flow in the area. The phenomenon is routine at branch sites, i.e. bifurcation and trifurcation of vessels or any multiple branching of a vessel. A common site of bifurcation of vessels is in the coronary vascular anatomy.

It is well known that the coronary arteries are markedly susceptible to atherosclerosis. This is especially true within the first six centimeters of origin of the vessel. Additionally, coronary arteries have multiple bifurcations. For example, the right and left coronary arteries bifurcate and branch as they descend the myocardium. Common sites for stenosis include the left coronary artery bifurcation to the circumflex and anterior interventricular (descending) artery; right coronary artery to the posterior interventricular and right marginal arteries; and bifurcations associated with the crux and marginal arteries. Further, any vessel of the body that suffers the effects of atherosclerosis can stenose and become a candidate for treatment, particularly in the peripheral vessels.

Treatment mechanisms for stenotic vessels have range from and include chemotherapy, radiation, Coronary Artery Bypass Grafting (CABG), angioplasty, rotational cutting devices to remove plaque formation and laser treatments. Each treatment has individual indications and contraindications. Additionally, each treatment modality has its own attendant risks. CABG of blocked or stenotic vessels is the least conservative, most expensive, most painful and is attended by the most serious complications. Surgery also requires the longest convalescence. See, Sutsch, Amamn, *To Stent or Not to Stent,* Schweiz. Med. Wochenchr. 1999; 129:1979–96. Chemotherapy and radiation treatment both have unwanted side effects. Currently, one of the safest and most effective treatments of stenotic vessels is percutaneous angioplasty. A common example of this is PTCA.

In the procedure, considered a non surgical interventional radiological procedure, a balloon catheter is placed in a diseased vessel through a small incision in to a main vessel; the femoral artery, for example. The catheter is tipped with a balloon at the end which can be inflated within the stenotic vessel to make the vessel patent. In order to guide the catheter to the diseased vessel and its stenosed portion, the catheter is placed over a steerable guide wire.

Inflation of the balloon is often all that is needed to make the stenotic vessel patent, but more often a stent is used to maintain patency of the vessel. A stent is a type of intravascular medical device used to maintain a bodily orifice or cavity after placement. Usually, a stent is comprised of an interconnected mesh of non-absorbable surgical grade material that, after placement, lies within the lumen of tubular structures and is used to provide support. Very commonly, a stent is used after dilation of an atherosclerotic coronary or peripheral vessel with a balloon catheter.

PTCA, with or without stent deployment, is performed commonly all over the world. Multiple vessels throughout the anatomy are treated. See, Sutsch, Amamn, *To Stent or Not to Stent,* Schweiz. Med. Wochenchr. 1999; 129:1979–96; Tan, Lim, *What you Need to Know— Coronary Stenting—What's New in the Horizon,* Singapore Med. J. 1999; Vol. 40(06). Treatment of bifurcation lesions is also common. See, Holmes et al., *Coronary Artery Stents,* JACC Vol. 32 No. 5, 1998:1471–82. Treatment of bifurcation lesions is associated with increased early complications including compromise of either the branch vessel (the vessel off the main or parent vessel) or the target lesion (usually the lesion in the parent vessel) and increased potential for restenosis because of inadequate initial results. Stenting has an additional potential problem in that it may impair access to the side branch.

Current practices for improving access to ostial lesions, elongated lesions, bifurcating lesions and other difficult to treat stenoses include multiple guide wires. The use of multiple guide wires can become entangled in the guiding catheter or within the vessel. Many procedures need to be aborted or delayed if the wires become hopelessly entangled; some cases are then moved to open heart surgery due to loss of stents in the coronary vessel or coronary occlusion from dissection. To maintain side branch access, "jailing guide wire technique" has been used in the past where the wire to the side branch artery is pinned between the stent and the vessel wall. If the jailed wire to the side branch artery is not needed, the wire is then removed and the stent further dilated. In addition to jailing the wire, there is also "jailing of the side branch artery access or origin" by the placement of stent across a bifurcating stenosis or a stenosis very close to a side branch artery. However, there is no guide wire in the side branch. But the opening of the side branch is covered with the stent. The side branch opening may be compromised by the struts of the stent, plaque shifting into the side branch or compression. These unwanted effects may acutely close the side branch manifesting as an acute myocardial infarction or later as restenosis from neointimal hyperplasia causing restriction in blood flow or ischemia. Treatment of the side branch next to the stenosis has been recognized as technically challenging for interventionalists as well as to patients. One goal of the current invention is to help eliminate and avoid these challenges.

Given the foregoing, a method and apparatus to avoid entanglement of guide wires, damage to vessels and better access to branch vessels will be a further advancement in the area of interventional procedures.

SUMMARY OF THE INVENTION

The present invention is directed to a method and apparatus for use in interventional medicine; particularly in multiple branch lesions located in the coronary and peripheral vasculature. The invention consists of a sheath containing single or multiple exitable lumens for the guidance of medical devices used in interventional medicine. The invention consists of exitable lumen guide wire sheaths wherein each sheath contains individually compartmentalized exitable lumens; each walled off from the other and each containing a mode of exit for the wire. Separation of the wires during that portion of the procedure prior to deployment of the stent or inflation of the balloon eliminates the risk of entanglement of multiple wires. A method for accomplishing this is introduced using the present invention to separate the wires prior to deployment and dilation of a balloon and stent or other selected intra-vascular medical device.

Each walled off lumen becomes a channel for travel of an individual guide wire. The first end of the sheath is located at the proximal portion, that portion that remains within the hands of the interventionalist or other practitioner. The first end of the sheath contains a feeder portion of greater durometer than the rest of the sheath. The feeder portion will have a channel corresponding to each individually compartmentalized lumen. The feeder portion will have an exitable portion along its length for the initial separation of a selected guide wire. The distal part of the exitable lumen guide wire sheath, that portion introduced percutaneously to the target lesion, is more flexible than the first end. In one preferred embodiment, the wall of the lumen can be opened along its length. In this way, a first selected guide wire may exit the sheath as a balloon and stent are advanced along its length or the sheath may be easily removed without losing wire position. The first selected guide wire is able to completely exit the individually compartmentalized exitable lumen as the end of the particular compartment may be selectively closed off at its distal end. Once the first selected wire and balloon are free of the sheath, the interventionalist or other practitioner may inflate and enlarge the stenotic lumen with the stent in a desired location. In another preferred embodiment, the distal second end of a selected exitable lumen of the exitable lumen guide wire sheath may be closed off and be distal to a pre-selected opening for directional advancement of a guide wire.

The first selected guide wire, having performed its function, allows for a second selected guide wire to be used without the risk of entanglement of the wires. The selected procedure may continue with additional guide wires without the risk of entanglement.

Other embodiments of the invention include differing fabrications of the wall of the individually compartmentalized lumens. Preferably, the design is directed to an ease of separation of the wire from the individually compartmentalized lumen. Scoring, weakening, fenestrating, and mold rolling the wall of the lumen are examples of such designs. This may be mounted, attached or fused to catheter balloon design(s).

Note that the figures and representations in the figures are not proportional and are for explanatory purposes only.

DETAILED DESCRIPTION OF THE INVENTION

The references cited above and below are hereby incorporated by reference as if fully set forth herein. The present invention involves a method and apparatus for use in interventional medicine.

Figure 1:
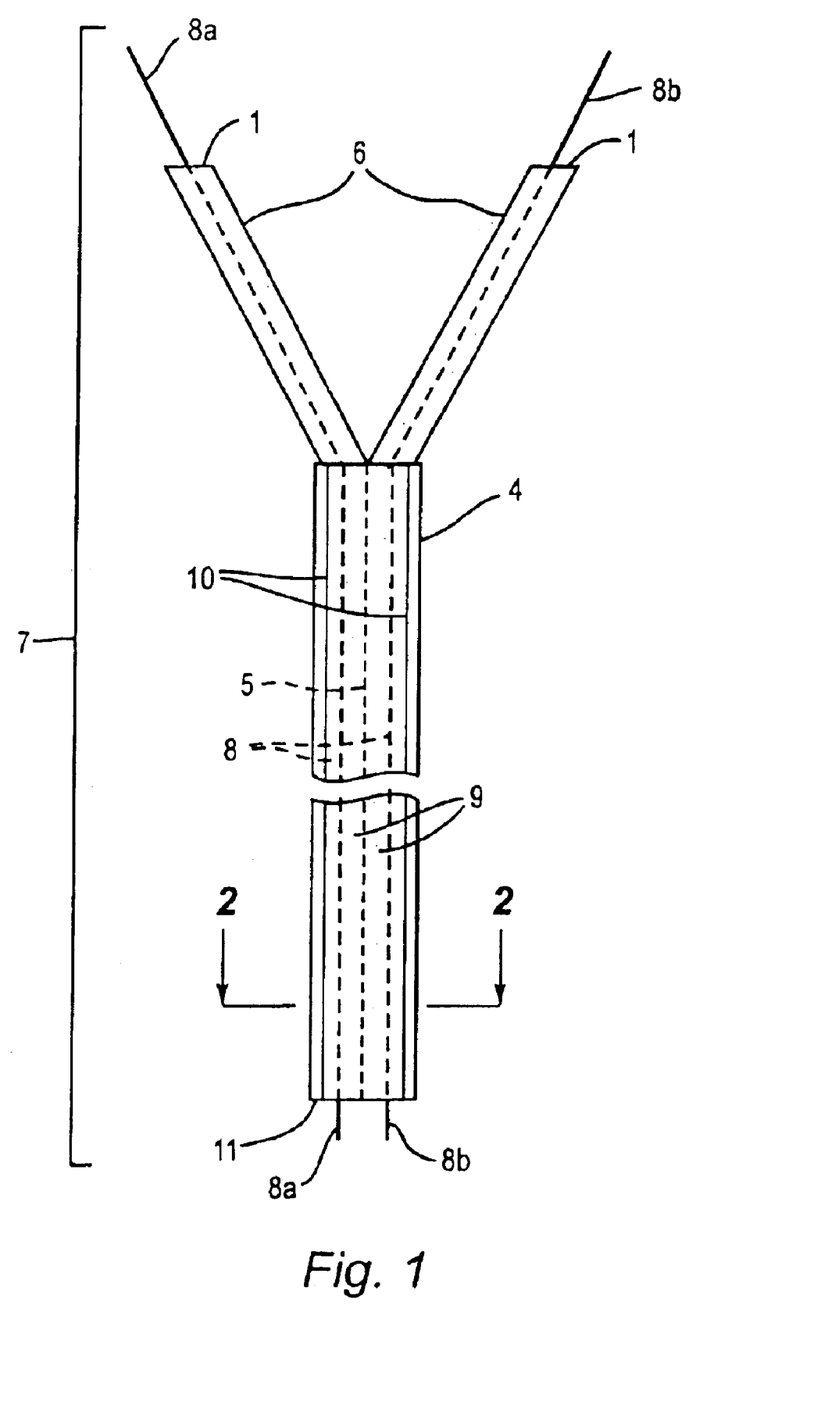
FIG. 1 is a diagrammatic representation of an exitable lumen guide wire sheath showing multiple lumens.
Figure 2:
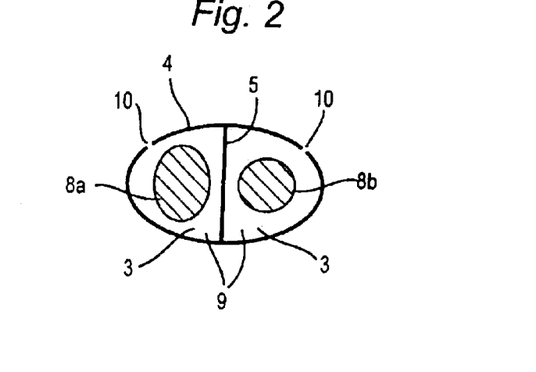
FIG. 2 is a cross section view of an embodiment of the invention showing an exit for the guide wires.

Referring to FIG. 1 and FIG. 2, the invention contains a first end 1 that is continuous with the number of individually compartmentalized lumens 3 in the flexible sheath 4. Individually compartmentalized lumens 3 are contained in a flexible sheath 4, each walled off from other individually compartmentalized lumens 3 by a division 5. The flexible sheath 4 is distal to the first end. The first end section of greater durometer is the feeder portion 6 of the exitable lumen guide wire sheath 7. It is from the feeder portion 6 of the exitable lumen guide wire sheath that the interventionalist or other practitioner is able to control the path and direct the course of the guide wire 8 (here shown as multiple guide wires 8a, 8b). This feeder portion 6 may be composed of, but is not limited to, any number of plastics, ceramics, rubber, and composite materials.

The first end 1 and feeder portion 6 are connected to a flexible sheath 4. The flexible sheath 4 is of a lesser durometer than the feeder portion 6. The flexible sheath 4 may contain a multiple of lumens 9. Each lumen contains or has an exit 10 for a guide wire 8 (8a, 8b) that extends from the first end 1 to the second end 11.

Figure 3:
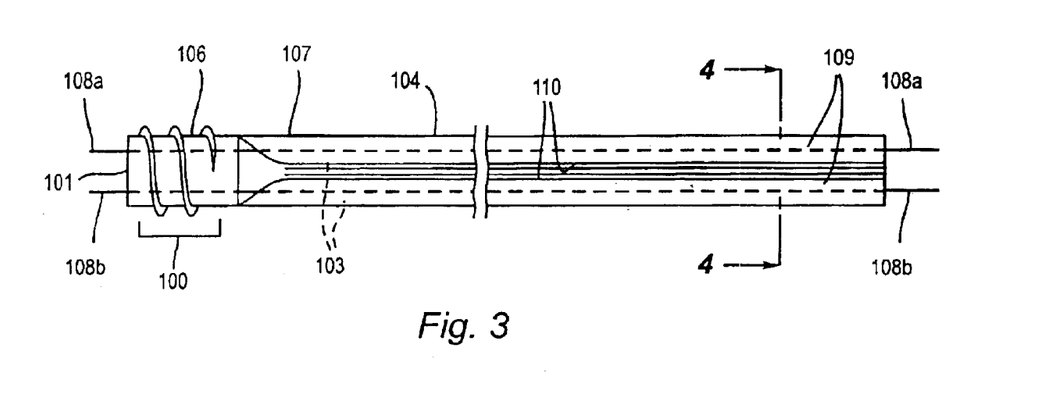
FIG. 3 illustrates a further embodiment of the invention showing a molded rolling of the flexible sheath.
Figure 4:
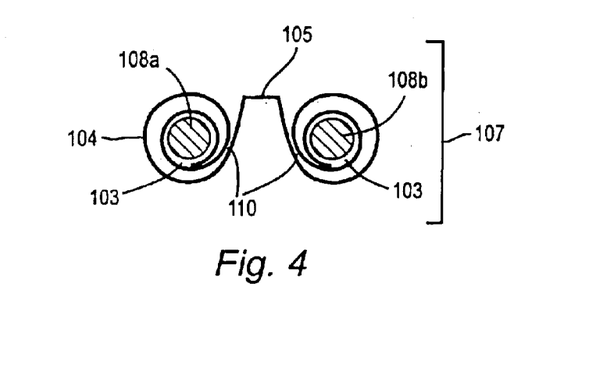
FIG. 4 is a cross section view of the embodiment of FIG. 3 showing the individually compartmentalized lumens formed by molded rolling of the flexible sheath.

FIG. 3 represents a further embodiment of the invention. Here, the individually compartmentalized lumens 103 are separated by molded rolling of the walls of the exitable lumen guide wire sheath 107. In this embodiment the first end 101 and feeder portion 106 contain a locking mechanism, for example, a Luer Lock section 100. FIG. 4 shows a cross section of this embodiment wherein the individually compartmentalized lumens 103 have been molded into a rolled configuration to provide for the exit 110 of the guide wire or guide wires in applications. For a bifurcation lesion, the flexible sheath 104 contains two coils that have been molded and rolled individually upon themselves to create a lumen 103 for a guide wire 108 (here shown as multiple guide wires 108a, 108b). A fold 105 in the middle of the flexible sheath 104 separates the individualized exitable lumens. The diameter can be approximately 1–2 mm to allow passage into a coronary or small peripheral vessel. Again, the guide wires, here a first 108a and a second guide wire 108b, will be back loaded into the flexible sheath 104. This could be accomplished during or before the intervention procedure. The center fold 105 of the mold rolled flexible sheath 104 separates the lumens. A first guide wire 108a may then be advanced to and advanced across target lesion #1 of a bifurcation lesion. The exitable lumen guide wire sheath 107 can then be advanced to target lesion #2 and the second guide wire 108b can be placed across lesion #2. At this stage, as above, the first 108a and second 108b wires are separate. As the interventionist advances an intra-vascular medical device toward each lesion, the molded roll would slightly unwind to accommodate the intra-vascular medical device, say a balloon catheter, while keeping the wires separate. The lesions may be treated, i.e., pre-dilated, and made ready for the bifurcating stents with two balloons. At this stage, both molded rolls in the flexible sheath 104 will uncoil as the stent and balloon in each lumen are advanced.

In other embodiments of the invention the exit 10 may be created by, but is not limited to, a series of fenestrations; a weakening in the wall of the flexible sheath that can be severed with the pressure from the forward advancement of an intra-vascular medical device along the wire; a folded over lapping section of flexible sheath; and, a molded rolling of the individually compartmentalized lumen upon itself that will separate as the intra-vascular medical device chosen is advanced along the wire.

In one embodiment of the invention an exitable lumen guide wire sheath is used and is combined with a balloon and stent arrangement 200. In this embodiment, depicted in FIG. 5a, a selected length of exitable lumen guide wire sheath 207 is inserted into a partially dilated stent 217 and then the stent 217 is then crimped (FIG. 5b) to capture the selected length of exitable lumen guide wire sheath 207. The balloon and stent arrangement 200, now containing the selected length of exitable lumen guide wire sheath 207, is clipped or otherwise coupled to a catheter shaft 250. The benefit of this particular embodiment will be addressed more completely in the examples that follow.

In one embodiment of the method and apparatus of the invention, the guide wires are back loaded in the distal second end 11 of the exitable lumen guide wire sheath 7 and out the feeder portion 6. Back loading refers to introduction of the guide wires 8 (8a, 8b) into the second end 11 of the flexible sheath 4 and advancing the exitable lumen guide wire sheath 7 toward a pre-identified lesion. After the guide wires 8 (8a, 8b) are in place, and the flexible sheath 4 has been introduced to a vessel through an incision, intravascular medical devices, such as a balloon catheter and stent, rotational cutting devices, laser apparatus or any number of intravascular medical devices used in vascular procedures can be advanced toward the lesion. The target lesion may be, but is not limited to, any stenotic vessel or cause of a stenotic vessel.

Figures 5A, 5B, 6, 7:
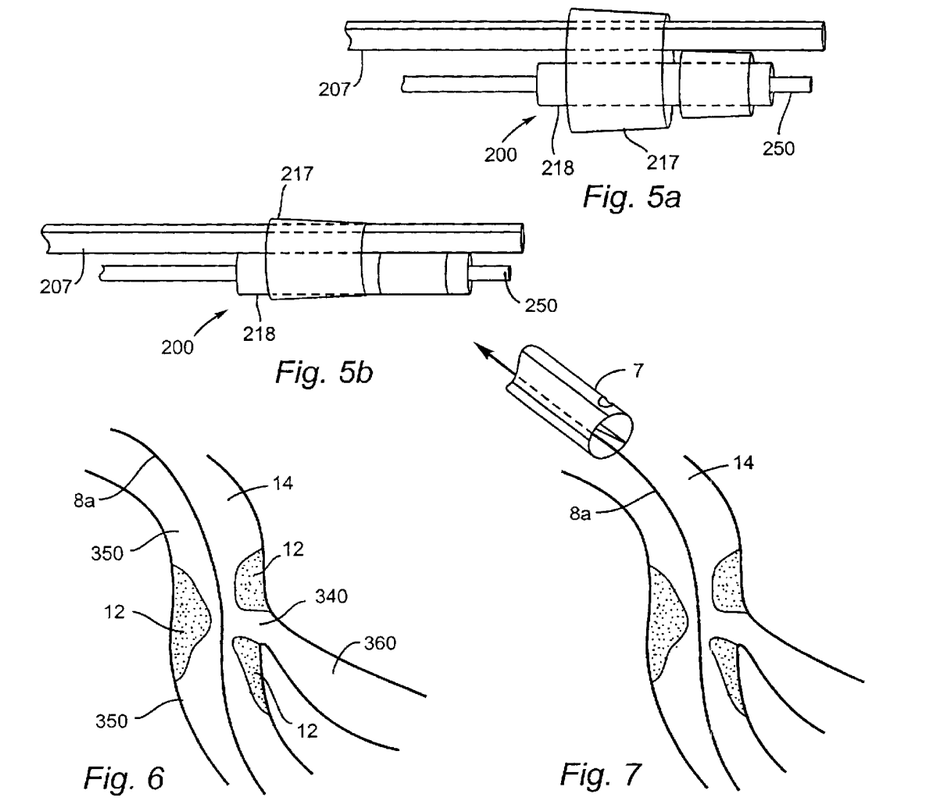
FIG. 5a illustrates a selected length of exitable lumen guide wire sheath inserted into a partially dilated stent.
FIG. 5b illustrates a selected length of exitable lumen guidewire sheath captured via a crimped stent.
FIG. 6 illustrates a bifurcation lesion example of a multiple branched lesion with a guide wire advanced in the main branch.
FIG. 7 illustrates the back loading of a first guide wire in to an exitable lumen guide wire sheath.

Once the target lesion is reached, a guide wire 8 is advanced through a selected part of the target lesion. For example, in a bifurcation lesion as depicted in FIG. 6, the first guide wire 308a may be advanced into the main branch 350 of a multiple branch lesion.

A further embodiment of the invention contains a prefabricated opening 16 at the distal end of the flexible sheath 4 just proximal to the second end. In this embodiment, a selected lumen or lumens is closed off at the second end 11. This allows directional advancement of a guide wire into a selected branch of a multiple branch lesion. Example IV, below, explains a use of this embodiment.

EXAMPLE I

Two Guide Wire PCTA Technique without Use of the Present Invention

The use of the two-guide wire method known in the art substantially reduces the risk of damage to a lateral branch, improves immediate dilatation of the major vessel, yet fails to affect the number of restenontic lesions in the late period. Further, problems of entanglement and increased neointimal hyperplasia are common. See, Abugov S A; Rudenko B A; Puretskii M V; Saakian Iu M; San'kov O V; Davydov S A; Belov Iu V; Sulimov, *A comparative analysis of the immediate and late results of coronary balloon angioplasty in bifurcation stenoses performed by the traditional method and by the "2-guide" method,* Vestn. Rentgenol. Radiol. 1998 July–August;(4): 10–4

To evaluate the efficiency of Percutaneous Transluminal Coronary Angioplasty (PTCA) for bifurcation stenoses, which had been made by the two-guide wire method, the results of angioplasties were examined in 147 patients with coronary heart disease. PTCA had been performed routinely in 54 patients and by the two-guide method in 32. Sixty-one patients who had undergone angioplasty for nonbifurcation lesions served as a control group. In the group of routine PTCA procedures, poor results with residual stenosis of the major vessel were seen in 13% of cases, the incidence of complications (dissection of unfavorable types, thrombosis of the major vessel) was 29.6%. In the two-guide wire PTCA technique, these indices were 15.6 and 2%, respectively, the incidence of restenosis was 46.9% and that of branch lesions was 6.3%. The high degree of restenosis is consistent with damage to the side branch vessel upon dilation of the major branch. Further, complications in two guide wire techniques are consistent with entanglement of the wires and damage to the intima due to snowplow effects and crossing and re-crossing of the stents and balloon. These findings lead to the conclusions that routine angioplasty of bifurcation stenoses yields poor early and late results of dilatation of lateral branches. Multi-guide wire techniques have advantages but are also attended by significant disadvantages. Routine PTCA and can be further improved using a exitable guide wire sheaths to avoid complications of entanglement and damage to the intima.

EXAMPLE II

Sequential Double Balloon Inflation without Use of the Present Invention

Bifurcation stenoses have been recognized to be at "high risk" for acute closure during Percutaneous Transluminal Coronary Angioplasty. See, Pinkerton C A; Slack J D *Complex coronary angioplasty: a dilatation of bifurcation stenoses.* Angiology 1985 August 36(8):543.

Use of the traditional single balloon technique in such situations often results in acute closure or worsening of the stenosis in the other branch. Again, this is a complication associated with dilation of a first, usually the parent, branch which results in a closure of the unprotected lateral branch. A technique utilizing simultaneous inflation of two balloons, ("kissing balloon" technique) has been utilized to avoid this complication. The kissing balloon technique uses a balloon advanced across both the main and side branch lesions. In this way, inflation of the balloon does not create collateral crushing of the branch vessel.

A double balloon technique has been developed using sequential inflations rather than simultaneous inflations to preserve the integrity of both branches while avoiding the arterial trauma produced by inflating two balloons in a small artery simultaneously. Twelve of 13 bifurcation stenoses were successfully treated with this sequential inflation double balloon technique. The initial results suggest high success when using a two-balloon technique. Greater efficacy and technical ease will be increased using an exitable lumen guidewire sheath, particularly in the embodiment using a selected length of exitable lumen guide wire. Using the technique of the present invention, balloons are located simultaneously in multiple branches thus avoiding the complications of closure of the collateral branches. Further, simultaneous inflation, when desired over sequential inflation, may also be accomplished.

EXAMPLE III

Use of Exitable Lumen Guide Wire Sheath in Dilation and Stenting

This example will demonstrate use of the exitable lumen guide wire sheath in the dilation and stenting of a bifurcation lesion.

Referring to FIG. 6, a diagrammatic representation of a bifurcation lesion 12 is shown. In this diagram, the lesion is distal and proximal to the side branch 360. It is a representation of a difficult to treat ostial type bifurcation lesion. As noted above, simple balloon dilation of the main branch 350 may close the ostium 340 of the side branch 360. Further, in a phenomenon known to those skilled in the art, the dilation of the parent lesion may create a "snowplow" effect. The snowplow effect is the unwanted movement of a plaque upon dilation of a vessel. To avoid these and other complications of treatment of bifurcation lesions noted above, an exitable lumen guide wire sheath is used.

FIG. 6 shows the placement of a first guidewire 8a through the main vessel 350 and lesion 12. The first guide wire 8a is seen to have been advanced through the proximal and distal portion of the lesion. At this time the first guide wire 8a is back loaded on to the exitable lumen guidewire sheath. Specifically, for this example, the exitable sheath is a multi-lumen exitable sheath. FIG. 7 illustrates this back loading of a first guidewire 8a on to an exitable multi-lumen sheath 7.

Figure 8:
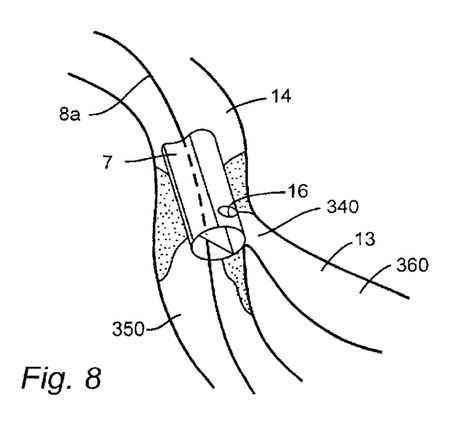
FIG. 8 illustrates the advancement of an exitable lumen guide wire sheath towards a target lesion.
Figure 9:
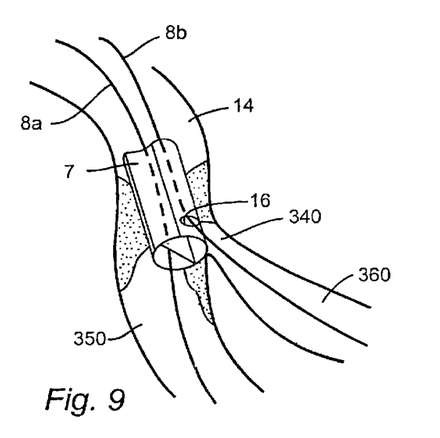
FIG. 9 illustrates the placement of a first guide wire and a second guide wire in a multiple branch lesion.

At this point the exitable multi-lumen guidewire sheath 7 is advanced along the first guide wire toward the bifurcation lesion 12. FIG. 8 demonstrates this position. For this type of lesion, proximal to the exitable multi-lumen guidewire sheath's second end 11 is a prefabricated opening 16 for directional advancement of a second guidewire 8b. FIG. 8 illustrates the placement of the first guide wire 8a and the second guide wire 8b. The interventionalist or other practitioner has the ability to steer the guide wires from the feeder portion 6 of the exitable multi-lumen guidewire sheath 7. As the second guide wire 8b is advanced to the distal end of the exitable multi lumen sheath 7, the guide wire is steered in to a prefabricated opening which has been carefully positioned at the ostium 340 of the side branch lesion. The second guide wire 8b is then advanced through the ostium 340 of the side branch vessel 360.

Figures 10, 11, 12, 13:
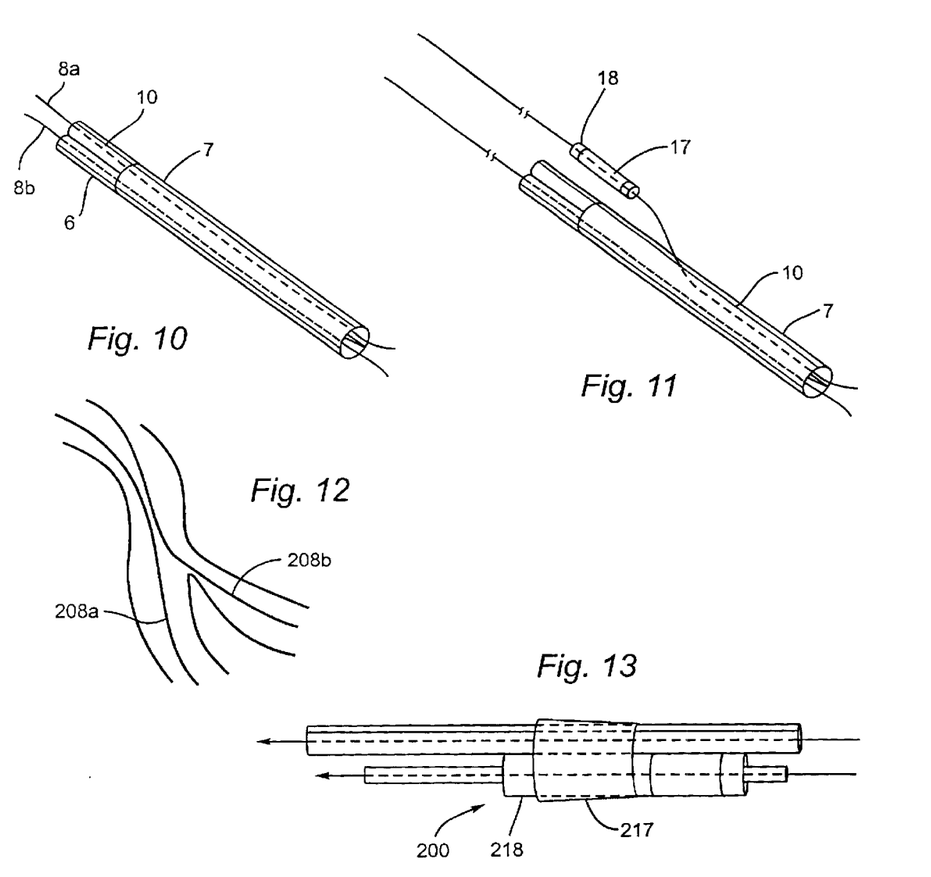
FIG. 10 illustrates a portion of exitable lumen guide wire sheath and mode of exit of guide wires through the exitable lumen.
FIG. 11 illustrates an example of an intra-vascular medical device displacing wires from the exitable lumen guide wire sheath.
FIG. 12 illustrates placement of a wire in the side branch, or the desired branch, of a multiple branch lesion.
FIG. 13 illustrates the back loading an intra-vascular medical device.

Another important advantage of the current invention, is that the multiple guide wires 8a, 8b are completely separate and are not entangled. FIG. 10 shows a portion of an exitable multi-lumen sheath 7. Further, FIG. 10 depicts the exitable property of the sheath. In this embodiment, the exitable property is achieved via a longitudinal slit 10.

At this point in the treatment of the bifurcation lesion the interventionalist or other practitioner manipulates either the first or second or both guide wires out of the exit provided in the feeder portion 6. An intra-vascular medical device, in this example a balloon catheter and stents, is back loaded at the proximal end of the guide wires. As is seen in FIG. 11, as the balloon 18 and stent 17 are advanced along the exitable multi-lumen guidewire sheath 7, the guide wires exit the sheath via the exitable portion 10. Further, a prefabricated opening 16 in an exitable lumen guide wire sheath may be employed for directional advancement of the guide wire. As mentioned, the opening 16 is just proximal to a selectively closed off second end of a selected exitable lumen guide wire sheath.

EXAMPLE IV

Protecting Access to the Side Branch in a Bifurcation Lesion Using Exitable Lumen Guide Wire Sheath The treatment of bifurcation lesions commonly causes closure of a side branch due to caging of the stent which makes it nearly impossible to enter the side branch lesion. This example describes the use of the method and apparatus of the present invention to protect access to the side branch, or a desired branch in a multiple branch lesion. In so doing, the embodiment depicted in FIGS. 5a and 5b will be beneficial.

It is advantageous to include a radio-opaque distal marker to the selected length of the exitable lumen guide wire sheath or of the balloon. For example, a very short marker would be placed longitudinally near the tip.

Again, an additional goal of an intervention procedure on a multi-branch lesion is to protect the side branch for access since an additional stent may cross it. As mentioned, current practice in cardiology has risks of caging the vessel so that wire access in the side branch may become impossible.

To decrease the risk, an exitable lumen guide wire sheath with, for example, a side slit, can be easily used to protect the side branch. These can be premounted by a manufacturer of the stent or placed by an interventionalist or other practitioner. It is, however, critical to pre-measure the amount of exitable lumen guidewire sheath to be used. This is also done, as is immediately apparent to those skilled in the art, by proper pre-identification and study of the target lesion; it is dependent on the placement of the lesion and its relation to the branch(es) as well as the branch(es) relation and angulation to the main vessel.

Referring to FIG. 12, the safest method is to place wires in the main vessel and the side branch that one seeks to protect. (If there were two branches, then three wires would have to be used along with the exitable multi-lumen sheath proposed.) The interventionalist or other practitioner can then predilate the lesions with balloons with the wires in place. Previously, the wire in the side branch 208b had to be removed prior to placing the stent so the wire would not be jailed or trapped behind the stent. In this method, the stent will be dilated partially, the exitable lumen guide wire sheath (here with a slit for the guide wire exit) will be placed through the stent (as mentioned, the length can be determined by the interventionalist, other practitioner or premanufactured).

Figure 14:
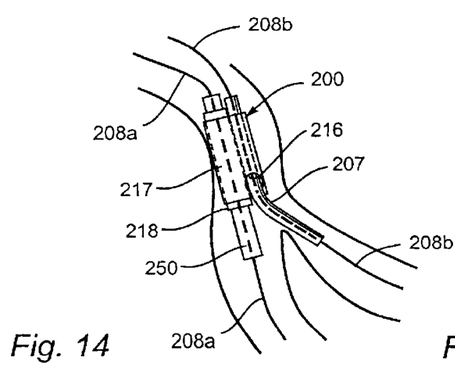
FIG. 14 illustrates the positioning of an intra-vascular medical device, here a stent.
Figure 15:
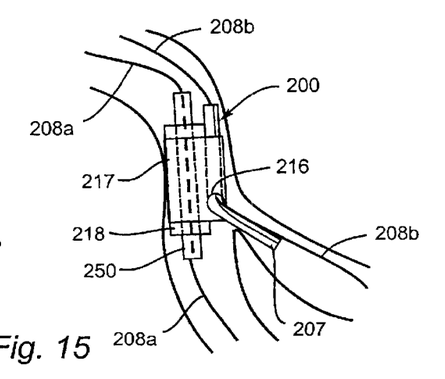
FIG. 15 illustrates the expansion of the stent in the multiple branch lesion.

The wires 208a, 208b are then back loaded into the lumens of the sheath and balloon as in FIG. 13. In the case where an embodiment of the invention containing a prefabricated opening 16 is used, only the first guide wire 8a is back loaded. The stent, balloon and the mounted sheaths 200 are advanced to the bifurcation. The stent 217 is positioned as depicted in FIG. 14. At this point there is still complete separation of the wires. The balloon 218 is inflated, expanding the stent 217 in to the wall of the vessel as in FIG. 15. The prefabricated opening 16, if this embodiment is used, is carefully placed by the interventionalist or other practitioner over the ostium of the branch to be treated.

At this point, any medical device needed may be advanced down the second guide wire 208b and the medical device will be directed passed or through the expanded stent 218. (Or the prefabricated opening if that embodiment is chosen.) As the medical device, say an additional stent, is advanced to meet the exitable lumen guide wire sheath it will pull the guide wire 208b away from the exitable lumen guide wire sheath while remaining separate from other wires. As described above and as depicted in FIG. 15, the wire will advance through the prefabricated opening. Throughout the method, safe and protected access to the side branch or desired branch is achieved.

The preceding examples demonstrate the apparatus and method of use for an exitable lumen guide wire sheath as well as suggesting alternate uses. Further, specific examples of comparisons with traditional treatments and studies are provided. These are only examples and are not intended to limit the invention to these examples. It is understood that modifying the examples above does not depart from the spirit of the invention. It is further understood that the examples can be applied on their own or in combination with each other.

What is claimed is:

1. A guide wire sheath for vascular procedures comprising:

a first end and a second end;

a feeder portion at the first end;

a flexible sheath distal to the first end and the feeder portion; and an exitable lumen in the feeder portion and the flexible sheath, wherein the feeder portion has a durometer that is greater than the durometer of the flexible sheath, and wherein the exitable lumen in the feeder portion comprises a non-intersecting cavity.

2. The guide wire sheath of claim 1 further comprising a plurality of exitable lumens.

3. The guide wire sheath of claim 2 wherein each of the plurality of exitable lumens is individually compartmentalized within the guide wire sheath.

4. The guide wire sheath of claim 3 wherein at least one of the plurality of exitable lumens further comprising an opening proximal to the second end and wherein at least one of the plurality of exitable lumens can be selectively closed off at the second end.

5. The guide wire sheath of claim 2 wherein the at least one of the plurality of exitable lumens is individually compartmentalized within the guide wire sheath.

6. The guide wire sheath of claim 1 wherein the exit from the exitable lumen is selected from the group consisting of a slit along the length of the individually compartmentalized lumen; a series of fenestrations along the length of the individually compartmentalized lumen; a scoring along the length of the individually compartmentalized lumen; mold rolling of the individually compartmentalized lumen upon itself along its length; overlapping but non-adhered section of flexible sheath of the individually compartmentalized lumen; and, selective thinning or weakening of the individually compartmentalized lumen along its length.

7. The guide wire sheath of claim 1 wherein the exitable lumen further comprising an opening proximal to the second end.

8. The guide wire sheath of claim 7 wherein the exitable lumen can be selectively closed off at the second end.

9. The guide wire sheath of claim 1 wherein the flexible sheath is of a flexibility so as to have essentially no structural support in the longitudinal direction whereby a guide wire is needed for support and advancement of at least a portion of the guide wire sheath into a catheter or for exchange.

10. The guide wire sheath of claim 9 wherein the walls of the exitable lumen are in a rolled configuration such that when the exitable lumen has received the guide wire the exitable lumen is in an unrolled state, and when the guide wire is not present in the exitable lumen the exitable lumen rolls back to a substantially collapsed state when compared to the exitable lumen containing the guide wire.

11. The guide wire sheath of claim 1 wherein the walls of the exitable lumen are in a rolled configuration such that when the exitable lumen has received the guide wire the exitable lumen is in an unrolled state, and when the guide wire is not present in the exitable lumen the exitable lumen rolls back to a substantially collapsed state when compared to the exitable lumen containing the guide wire.

12. The guide wire sheath of claim 1 wherein the exitable lumen further comprising a continuous or non-continuous exit along the length of the exitable lumen in at least a portion of the feeder portion and at least a portion of the flexible sheath.

13. The guide wire sheath of claim 12 wherein the exitable lumen comprises an exit along the entire length of the feeder portion.

14. A guide wire sheath comprising:
   a first end and a second end;
   a feeder portion at the first end;
   a flexible sheath distal to the first end and the feeder portion; and
   an exitable lumen in the feeder portion and the flexible sheath,
   wherein the exitable lumen comprises a continuous or non-continuous exit along the length of the exitable lumen in at least a portion of the feeder portion and in at least a portion of the flexible sheath.

15. The guide wire sheath of claim 14 wherein the feeder portion has a durometer that is greater than the durometer of the flexible sheath.

16. The guide wire sheath of claim 15 wherein the exitable lumen comprises an exit along the entire length of the feeder portion.

17. The guide wire sheath of claim 16 the wherein the guide wire sheath further comprising a plurality of exitable lumens.

18. The guide wire sheath of claim 17 wherein at least one of the plurality of exitable lumens is individually compartmentalized within the guide wire sheath.

19. The guide wire sheath of claim 18 wherein at least one of the plurality of exitable lumens further comprising an opening proximal to the second end.

20. The guide wire sheath of claim 19 wherein at least one of the plurality of exitable lumens can be selectively closed off at the second end.

21. The guide wire sheath of claim 15 wherein the exit from the exitable lumen is selected from the group consisting of a slit or slits along the length of the individually compartmentalized lumen; a series of fenestrations along the length of the individually compartmentalized lumen; a scoring along the length of the individually compartmentalized lumen; mold rolling of the individually compartmentalized lumen upon itself along its length; overlapping but non-adhered section of flexible sheath of the individually compartmentalized lumen; and, selective thinning or weakening of the individually compartmentalized lumen along its length.

22. The guide wire sheath of claim 15 wherein the exitable lumen is configured for receiving a guide wire and wherein the walls of the exitable lumen are in a rolled configuration such that when the exitable lumen has received the guide wire the exitable lumen is in an unrolled state, and when the guide wire is not present in the exitable lumen the exitable lumen rolls back to a substantially collapsed state when compared to the exitable lumen containing the guide wire.

23. The guide wire sheath of claim 22 wherein the flexible sheath is of a flexibility so as to have essentially no structural support in the longitudinal direction whereby a guide wire is needed for support and advancement of at least a portion of the guide wire sheath into a catheter or for exchange.

24. The guide wire sheath of claim 15 wherein the flexible sheath is of a flexibility so as to have essentially no structural support in the longitudinal direction whereby a guide wire is needed for support and advancement of at least a portion of the guide wire sheath into a catheter or for exchange.

25. The guide wire sheath of claim 14 wherein the exitable lumen in the feeder portion comprises a non-intersecting cavity.

26. A guide wire sheath comprising:
   an exitable lumen for receiving a guide wire wherein the walls of the exitable lumen are configured in a rolled configuration such that when the exitable lumen has received the guide wire the exitable lumen is in an unrolled state, and when the guide wire is not present in the exitable lumen the exitable lumen rolls back to a substantially collapsed state when compared to the exitable lumen containing the guide wire.

27. The guide wire sheath of claim 26 wherein the flexible sheath is of a flexibility so as to have essentially no structural support in the longitudinal direction whereby a guide wire is needed for support and advancement of at least a portion of the guide wire sheath into a catheter or for exchange.

* * * * *